United States Patent
Sheldon et al.

(10) Patent No.: US 11,045,336 B2
(45) Date of Patent: *Jun. 29, 2021

(54) SECURED STRAND END DEVICES

(71) Applicant: IDev Technologies, Inc., Santa Clara, CA (US)

(72) Inventors: Jeffery Sheldon, League City, TX (US); Richard Booth, Friendswood, TX (US); Kenneth M. Bueche, Friendswood, TX (US)

(73) Assignee: IDev Technologies, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/668,521

(22) Filed: Oct. 30, 2019

(65) Prior Publication Data

US 2020/0060853 A1 Feb. 27, 2020

Related U.S. Application Data

(60) Continuation of application No. 15/489,521, filed on Apr. 17, 2017, now Pat. No. 10,470,902, which is a
(Continued)

(51) Int. Cl.
| | |
|---|---|
| *A61F 2/06* | (2013.01) |
| *A61F 2/88* | (2006.01) |
| *B23K 26/244* | (2014.01) |
| *B23K 26/20* | (2014.01) |
| *A61F 2/95* | (2013.01) |
| *A61F 2/90* | (2013.01) |
| *D04C 1/06* | (2006.01) |
| *D06C 7/00* | (2006.01) |

(Continued)

(52) U.S. Cl.
CPC .............. *A61F 2/885* (2013.01); *A61F 2/06* (2013.01); *A61F 2/844* (2013.01); *A61F 2/86* (2013.01); *A61F 2/90* (2013.01); *A61F 2/91* (2013.01); *A61F 2/915* (2013.01); *A61F 2/95* (2013.01); *A61F 2/966* (2013.01); *B23K 26/20* (2013.01); *B23K 26/244* (2015.10); *D03D 3/02* (2013.01); *D04C 1/06* (2013.01); *D06C 7/00* (2013.01); *A61F 2002/061* (2013.01); *A61F 2002/91591* (2013.01); *A61F 2002/9534* (2013.01); *A61F 2002/9665* (2013.01); *A61F 2210/0014* (2013.01); *A61F 2220/0058* (2013.01); *B23K 2101/32* (2018.08); *B23K 2103/14* (2018.08); *D10B 2509/00* (2013.01); *D10B 2509/06* (2013.01); *Y10T 29/49849* (2015.01)

(58) Field of Classification Search
CPC .... A61F 2/86; A61F 2/966; A61F 2/06; A61F 2/95; A61F 2/90; A61F 2220/0058; A61F 2002/061; A61F 2002/9665; A61F 2002/9534; D04C 1/06; D03D 41/00; D03D 3/02; D06C 7/00; B23K 26/20; B23K 2203/14; B23K 2201/32; Y10T 29/49849; D10B 2509/06
See application file for complete search history.

(56) References Cited

U.S. PATENT DOCUMENTS

| | | | | |
|---|---|---|---|---|
| 6,632,241 | B1 * | 10/2003 | Hancock | A61B 17/12022 128/898 |
| 2005/0256563 | A1 * | 11/2005 | Clerc | A61F 2/90 623/1.16 |

* cited by examiner

*Primary Examiner* — Jun S Yoo
(74) *Attorney, Agent, or Firm* — Fulwider Patton LLP

(57) ABSTRACT

Methods for securing strand ends of devices configured for insertion into an anatomical structure, and the resulting devices.

10 Claims, 11 Drawing Sheets

Related U.S. Application Data continuation of application No. 15/331,667, filed on Oct. 21, 2016, now Pat. No. 9,629,736, which is a continuation of application No. 15/229,844, filed on Aug. 5, 2016, now Pat. No. 9,585,776, which is a continuation of application No. 15/001,117, filed on Jan. 19, 2016, now Pat. No. 9,408,730, which is a continuation of application No. 14/601,152, filed on Jan. 20, 2015, now Pat. No. 9,408,729, which is a division of application No. 14/289,519, filed on May 28, 2014, now Pat. No. 8,966,733, which is a continuation of application No. 14/260,213, filed on Apr. 23, 2014, now Pat. No. 9,149,374, which is a division of application No. 13/549,334, filed on Jul. 13, 2012, now Pat. No. 8,739,382, which is a continuation of application No. 11/876,666, filed on Oct. 22, 2007, now Pat. No. 9,895,242.

(60) Provisional application No. 60/862,456, filed on Oct. 22, 2006.

(51) Int. Cl.

| | | |
|---|---|---|
| *A61F 2/966* | (2013.01) | |
| *A61F 2/86* | (2013.01) | |
| *A61F 2/844* | (2013.01) | |
| *D03D 3/02* | (2006.01) | |
| *A61F 2/91* | (2013.01) | |
| *A61F 2/915* | (2013.01) | |
| *B23K 101/32* | (2006.01) | |
| *B23K 103/14* | (2006.01) | |

| Stent Internal Dia. (mm) | Wire Dia. (in.) | Coupling Structure Length (in.) | Coupling Structure Internal Dia. (in.) | Coupling Structure External Dia. (in.) | Frequency (Hertz) | Peak Power (Watts) | Pulse Duration (milli-seconds) | A-scale (Lasag pulse compensation factor) | Argon Flow Rate (scfh) |
|---|---|---|---|---|---|---|---|---|---|
| 4.0000 | 0.0060 | 0.0700 | 0.0070 | 0.0090 | 10 | 200 | 0.25 | 120 | 5 |
| 5.0000 | 0.0060 | 0.0800 | 0.0070 | 0.0090 | 10 | 200 | 0.25 | 120 | 5 |
| 6.0000 | 0.0070 | 0.1000 | 0.0075 | 0.0105 | 10 | 200 | 0.30 | 100 | 5 |
| 7.0000 | 0.0070 | 0.1000 | 0.0075 | 0.0105 | 10 | 200 | 0.30 | 100 | 5 |
| 8.0000 | 0.0080 | 0.1200 | 0.0085 | 0.0120 | 10 | 200 | 0.30 | 100 | 5 |
| 9.0000 | 0.0080 | 0.1500 | 0.0085 | 0.0120 | 10 | 200 | 0.30 | 100 | 5 |
| 10.0000 | 0.0080 | 0.1500 | 0.0085 | 0.0120 | 10 | 200 | 0.30 | 100 | 5 |

| Internal Stent Dia. 0.5 (mm) | Stent Length (mm) | Nitinol Wire Dia. (in.) | Coupling Structure Code | A (in.) | B (in.) | C (in.) |
|---|---|---|---|---|---|---|
| 4.0 | 40 | 0.006 | -01 | 0.010 | 0.005 | 0.010 |
| 4.0 | 60 | 0.006 | -01 | 0.010 | 0.005 | 0.010 |
| 4.0 | 80 | 0.006 | -01 | 0.010 | 0.005 | 0.010 |
| 5.0 | 40 | 0.006 | -02 | 0.010 | 0.005 | 0.010 |
| 5.0 | 60 | 0.006 | -02 | 0.010 | 0.005 | 0.010 |
| 5.0 | 80 | 0.006 | -02 | 0.010 | 0.005 | 0.010 |
| 5.0 | 100 | 0.006 | -02 | 0.010 | 0.005 | 0.010 |
| 5.0 | 120 | 0.006 | -02 | 0.010 | 0.005 | 0.010 |
| 6.0 | 40 | 0.007 | -03 | 0.015 | 0.008 | 0.010 |
| 6.0 | 60 | 0.007 | -03 | 0.015 | 0.008 | 0.010 |
| 6.0 | 80 | 0.007 | -03 | 0.015 | 0.008 | 0.010 |
| 6.0 | 100 | 0.007 | -03 | 0.015 | 0.008 | 0.010 |
| 6.0 | 120 | 0.007 | -03 | 0.015 | 0.008 | 0.010 |
| 7.0 | 40 | 0.007 | -03 | 0.015 | 0.008 | 0.010 |
| 7.0 | 60 | 0.007 | -03 | 0.015 | 0.008 | 0.010 |
| 7.0 | 80 | 0.007 | -03 | 0.015 | 0.008 | 0.010 |
| 7.0 | 100 | 0.007 | -03 | 0.015 | 0.008 | 0.010 |
| 7.0 | 120 | 0.007 | -03 | 0.015 | 0.008 | 0.010 |
| 8.0 | 40 | 0.008 | -04 | 0.015 | 0.008 | 0.010 |
| 8.0 | 60 | 0.008 | -04 | 0.015 | 0.008 | 0.010 |
| 8.0 | 80 | 0.008 | -04 | 0.015 | 0.008 | 0.010 |
| 8.0 | 100 | 0.008 | -04 | 0.015 | 0.008 | 0.010 |
| 8.0 | 120 | 0.008 | -04 | 0.015 | 0.008 | 0.010 |
| 9.0 | 40 | 0.008 | -05 | 0.020 | 0.008 | 0.010 |
| 9.0 | 60 | 0.008 | -05 | 0.020 | 0.008 | 0.010 |
| 10.0 | 40 | 0.008 | -05 | 0.020 | 0.008 | 0.010 |
| 10.0 | 60 | 0.008 | -05 | 0.020 | 0.008 | 0.010 |
| 5.0 | 150 | 0.006 | -02 | 0.010 | 0.005 | 0.010 |
| 6.0 | 150 | 0.007 | -03 | 0.015 | 0.008 | 0.010 |
| 7.0 | 150 | 0.007 | -03 | 0.015 | 0.008 | 0.010 |

*FIG. 14B*

SECURED STRAND END DEVICES

CROSS-REFERENCE(S) TO RELATED APPLICATION(S)

This application is a continuation of U.S. application Ser. No. 15/489,521, filed Apr. 17, 2017, which is a continuation of U.S. application Ser. No. 15/331,667, filed Oct. 21, 2016, now U.S. Pat. No. 9,629,736, issued Apr. 25, 2017, which is a continuation of U.S. application Ser. No. 15/229,844, filed Aug. 5, 2016, now U.S. Pat. No. 9,585,776, issued Mar. 7, 2017, which is a continuation of U.S. application Ser. No. 15/001,117, filed Jan. 19, 2016, now U.S. Pat. No. 9,408,730, issued Aug. 9, 2016, which is a continuation of U.S. application Ser. No. 14/601,152, filed Jan. 20, 2015, now U.S. Pat. No. 9,408,729, issued Aug. 9, 2016, which is a divisional of U.S. application Ser. No. 14/289,519, filed May 28, 2014, now U.S. Pat. No. 8,966,733, issued Mar. 3, 2015, which is a continuation of U.S. application Ser. No. 14/260,213, filed Apr. 23, 2014, now U.S. Pat. No. 9,149,374, issued Oct. 6, 2015, which is a divisional of U.S. application Ser. No. 13/549,334, filed Jul. 13, 2012, now U.S. Pat. No. 8,739,382, issued Jun. 3, 2014, which is a continuation of U.S. application Ser. No. 11/876,666, filed Oct. 22, 2007, now U.S. Pat. No. 9,895,242, issued Feb. 20, 2018, which claims priority benefit of U.S. Provisional App. No. 60/862,456, filed Oct. 22, 2006, all of which applications are hereby incorporated by reference in their entirety.

BACKGROUND

1. Field

The present invention relates generally techniques and structures for securing the ends of strands, such as wires, of devices suited for placement in anatomical structures, and the resulting devices. Examples of such devices include woven, self-expanding stents.

2. Description of Related Art

Examples of devices suitable for insertion into an anatomical structure that are created from one or more strands are found in U.S. Pat. Nos. 6,007,574; 6,419,694; and 7,018,401; and in U.S. Patent Application Publication Nos. US 2005/0049682 and US 2006/0116752, all of which are incorporated by reference.

SUMMARY OF THE INVENTION

Some embodiments of the present methods include securing a coupling structure to a first strand end portion of a device configured for insertion into an anatomical structure; and securing the coupling structure to a second strand end portion of the device; where the first and second strand end portions are substantially aligned, the coupling structure is not a strand of the device, and the device includes one or more strands that include nickel and titanium. In some embodiments, the length of the coupling structure is less than 25, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 percent of the length of the device; this may be true for each coupling structure that is used. The coupling structure may be configured such that it has a passageway before it is secured to the first and second strand portions, and it may be placed into direct contact with the first and second strand end portions prior to the securing. The device may be a stent (e.g., a stent woven from multiple strands), or any other medical device suited for use in treating a patient, such as a filter or an occluder. The device may be self-expanding. The device may have two or more device ends (such as the two ends of a straight stent or the three ends of a bifurcated stent), and each device end may be characterized by or defined by strand bends, where the strand bends of a given device end are similar (e.g., substantially similar) in shape to at least each other and in some instances to all of the strand bends of all the device ends, such that one device end looks very similar to the other device end or device ends. The number of coupling structures that are used may correspond to the number of strands (e.g., wires) that are used to create the device, and they may be positioned in axial alignment (parallel to the longitudinal axis of the device) or they may be axially offset from each other and positioned around the circumference of the device. The securing may be accomplished by welding (e.g., laser welding) the coupling structure to the first strand end portion to create a first welded region and by welding the coupling structure to the second strand end portion to create a second welded region. The two welded regions may be separated from each and unconnected by any other welded region. The two strand end portions directly touch each other in some embodiments, and in other embodiments are not in direct contact with each other. The strand end portions may be substantially aligned with each other (end-to-end), or they may be positioned in side-by-side relationship (which may be characterized as overlapping). In some embodiments, the coupling structure is a piece of material that is separate from the first strand end portion and from the second strand end portion and, when a weld is used to accomplish the securing, is placed into direct contact with both strand end portions before the welding begins. In some embodiments, some or all of the securing steps result in a given half of a given strand being secured to either (a) only one other strand or (b) only the other half of the same strand. In some embodiments, the coupling structure is positioned beneath a strand that crosses over it. In some embodiments, all coupling structures that are used are positioned in this same fashion. In some embodiments, neither the coupling structure nor the strand end portions to which it is secured undergo a smoothing step after the securing is complete. In some embodiments where the device is woven from multiple strands such that strand crossings are created defining obtuse angles that increase when the device is axially compressed from an unconstrained state, each device opening (other than the openings that border the longitudinal passageway or passageways of the device) is defined by at least three strand crossings, where each strand crossing is defined by two crossed strand portions. In some embodiments, the coupling structure positioned nearest to a particular end of the device (a "device end") is spaced apart from all device ends (even at the portion of the coupling structure nearest the device end in question) by at least one strand crossing (in some embodiments, by at least two strand crossings; in some embodiments, by at least three strand crossings; in some embodiments, by at least four strand crossing; in some embodiments, by at least five strand crossings) in a direction (e.g., along a line) that is substantially parallel with a longitudinal axis of the device.

Some embodiments of the present methods include welding a coupling structure to a first strand end portion of a device configured for insertion into an anatomical structure; and welding the coupling structure to a second strand end portion of the device; where the coupling structure is not a strand of the device, and the device includes one or more strands that include nickel and titanium.

The present devices may have one or more strands and be configured for insertion into an anatomical structure. In some embodiments, the present devices include a coupling structure secured to two different strand end portions that are substantially aligned with each other; where the two different strand end portion includes nickel and titanium, and the coupling structure is not a strand of the device. In some embodiments, the present devices include a coupling structure welded to two different strand end portions; where the two different strand end portion includes nickel and titanium, and the coupling structure is not a strand of the device. The device may be a stent, or any other medical device suited for use in treating a patient, such as a filter or an occluder. The number of coupling structures that are used may correspond to the number of strands (e.g., wires) the device has, and they may be positioned in axial alignment (parallel to the longitudinal axis of the woven device) or they may be axially offset from each other and positioned around the circumference of the device. The strand end portions in each pair that are secured with (e.g., welded to) a given coupling structure may be substantially aligned with each other or they may be placed in side-by-side relationship with each other (which may be characterized as overlapping). In some embodiments, the length of the coupling structure is less than 25, 24, 23, 22, 21, 20, 19, 18, 17, 16, 15, 14, 13, 12, 11, 10, 9, 8, 7, 6, 5, 4, 3, 2, 1, 0.9, 0.8, 0.7, 0.6, 0.5, 0.4, 0.3, 0.2, or 0.1 percent of the length of the device; this may be true for each coupling structure that is used. The coupling structure may be configured such that it has a passageway before it is secured to the first and second strand portions, and it may be placed into direct contact with the first and second strand end portions prior to being secured (e.g., welded). The device may be a stent (e.g., a stent woven from multiple strands), or any other medical device suited for use in treating a patient, such as a filter or an occluder. The device may be self-expanding. The device may have two or more device ends (such as the two ends of a straight stent or the three ends of a bifurcated stent), and each device end may be characterized by or defined by strand bends, where the strand bends of a given device end are similar (e.g., substantially similar) in shape to at least each other and in some instances to all of the strand bends of all the device ends, such that one device end looks very similar to the other device end or device ends. The number of coupling structures that are used may correspond to the number of strands (e.g., wires) that are used to create the device, and they may be positioned in axial alignment (parallel to the longitudinal axis of the device) or they may be axially offset from each other and positioned around the circumference of the device. The coupling structure may be secured to the first strand end portion by a weld that forms a first welded region, the coupling structure is secured to the second strand end portion by a weld that forms a second welded region, and the first and second welded regions are not directly connected to each other by another welded region. The two welded regions may be separated from each and unconnected by any other welded region. The two strand end portions directly touch each other in some embodiments, and in other embodiments are not in direct contact with each other. In some embodiments, the coupling structure is a piece of material that is separate from the first strand end portion and from the second strand end portion and, when a weld is used to secure the coupling structure to those strand end portions, is placed into direct contact with both strand end portions before the welding begins. In some embodiments, a given half of a given strand of the device is secured to either (a) only one other strand or (b) only the other half of the same strand. In some embodiments, the coupling structure is positioned beneath a strand that crosses over it. In some embodiments, all coupling structures that are used are positioned in this same fashion. In some embodiments, neither the coupling structure nor the strand end portions to which it is secured require smoothing after being secured. In some embodiments where the device is woven from multiple strands such that strand crossings are created defining obtuse angles that increase when the device is axially compressed from an unconstrained state, each device opening (other than the openings that border the longitudinal passageway or passageways of the device) is defined by at least three strand crossings, where each strand crossing is defined by two crossed strand portions. In some embodiments, the coupling structure positioned nearest to a particular end of the device (a "device end") is spaced apart from all device ends (even at the portion of the coupling structure nearest the device end in question) by at least one strand crossing (in some embodiments, by at least two strand crossings; in some embodiments, by at least three strand crossings; in some embodiments, by at least four strand crossing; in some embodiments, by at least five strand crossings) in a direction (e.g., along a line) that is substantially parallel with a longitudinal axis of the device.

Details associated with these embodiments and others are provided below.

BRIEF DESCRIPTION OF THE DRAWINGS

The following drawings illustrate by way of example and not limitation. Identical reference numerals do not necessarily indicate an identical structure. Rather, the same reference numeral may be used to indicate a similar feature or a feature with similar functionality. Not every feature of each embodiment is labeled in every figure in which that embodiment appears, in order to keep the figures clear.

FIG. 14B is a table containing example values for the dimensions depicted in FIG. 14A and other aspects of a stent created according to the present methods.

DESCRIPTION OF ILLUSTRATIVE EMBODIMENTS

Figure 1:
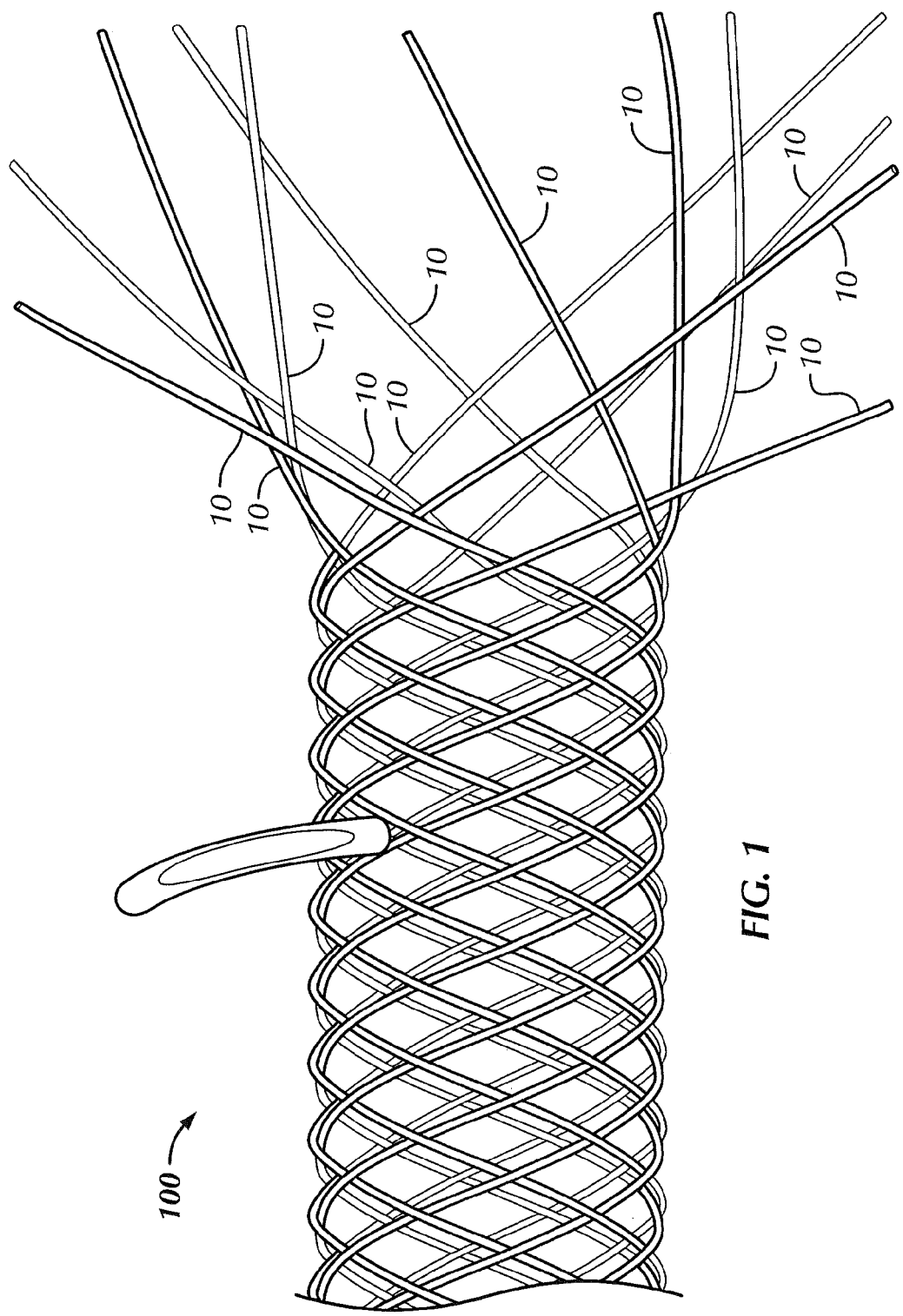
FIG. 1 shows an example of a portion of a device that is being configured for insertion into an anatomical structure, and at a stage of creation where free strand ends are positioned at one end of the device. There is a hook depicted in the top, central portion of the figure that is holding the device to an underlying surface. The hook is not part of the device.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a device or method that "comprises," "has," "contains," or "includes" one or more elements possesses those one or more elements, but is not limited to possessing only those one or more elements or steps. Likewise, an element of a device or a step of a method that "comprises," "has," "contains," or "includes" one or more features possesses those one or more features, but is not limited to possessing only those one or more features. Furthermore, a structure that is configured in a certain way must be configured in at least that way, but also may be configured in a way or ways that are not specified.

Any embodiment of any of the present methods and devices may consist of or consist essentially of—rather than comprise/include/contain/have—the described steps and/or features. Thus, and by way of example, while some embodiments of the present methods comprise welding a coupling structure to a first strand end portion of a device configured for insertion into an anatomical structure; and welding the coupling structure to a second strand end portion of the device; where the coupling structure is not a strand of the device, and the device includes one or more strands that include nickel and titanium, other embodiments consist essentially of or consist of welding a coupling structure to a first strand end portion of a device configured for insertion into an anatomical structure; and welding the coupling structure to a second strand end portion of the device; where the coupling structure is not a strand of the device, and the device includes one or more strands that include nickel and titanium.

The terms "a" and "an" are defined as one or more than one unless this disclosure explicitly requires otherwise. The terms "substantially" and "about" are defined as at least close to (and include) a given value or state (preferably within 10% of, more preferably within 1% of, and most preferably within 0.1% of).

The present methods may be used to secure two unsecured strand ends of a device configured for insertion into an anatomical structure. The initial process used to create the device may involve weaving—such as the weaving techniques disclosed in U.S. Pat. Nos. 6,792,979 and 7,048,014, which are incorporated by reference—or any other process that results in at least two unsecured strand ends. If weaving is used, one suitable braiding machine that may be used is the Steeger 24 Carrier Horizontal Fine Wire Carrier Braider HS 140-24-IH manufactured by Steeger USA (Spartanburg, S.C.). The device may be created from one or more strands, and it may have a variety of configurations, such as stent (e.g., one with two ends or a multi-legged stent with more than two ends), an occluder, or a filter. The strand ends may be secured with a coupling structure that includes a passageway (such as a small tube) into which the strand ends can be inserted from opposite ends and that is welded (e.g., laser welded) to the strand end portions inserted into it. However, the coupling structure need not encompass the strand ends, as a small tube does. Instead, in other embodiments, the coupling structure could comprise a flat strip to which the strand ends are coupled, or a strip that is contoured, such as a portion of a small tube. Furthermore, though laser welding is discussed below as a preferred joining technique, other techniques may be used, including (but not limited to) electron beam welding, resistance welding, tungsten inert gas welding, metal inert gas welding, crimping, soldering, braising, and gluing.

The coupling structure may be made from the same materials as the strand end portions to which it is coupled (e.g., a nickel-titanium coupling structure may be used to couple two nickel-titanium strand end portions together), or it may be made from a different material or materials (e.g., a stainless steel coupling structure may be used to couple two nickel-titanium strand end portions together).

In embodiments in which is woven from nickel-titanium wires (nickel—56.0 percent by weight of the total composition; titanium—balance of the total composition), and the initial weaving is complete, the device (with the mandrel on which it was formed, if desired) can be heat treated according to the information in Table 1 below:

TABLE 1

| Stent Diameter (mm) | Furnace Temperature Setting (° C.) | Heat Treatment Time (minutes) |
|---|---|---|
| 4.0 | 525 | 5 |
| 5.0 | 535 | 5 |
| 6.0 | 510 | 10 |
| 7.0 | 520 | 10 |
| 8.0 | 510 | 13 |

TABLE 1-continued

| Stent Diameter (mm) | Furnace Temperature Setting (° C.) | Heat Treatment Time (minutes) |
|---|---|---|
| 9.0 | 520 | 13 |
| 10.0 | 530 | 13 |

The device may have free strand ends positioned at some or all of the ends of the device when it is heat treated in this fashion. FIG. 1 shows an example of a device (device 100) that has one or more strands and is configured for insertion into an anatomical structure. Device 100, which is a stent, was created woven according to techniques disclosed in U.S. Pat. No. 7,018,401 from six strands (wires) that possess twelve strand halves 10. There are no free strand ends at the device end of device 100 that is not shown. Each half strand was secured (see, e.g., FIG. 3) to only one other half strand (which either belonged to the same or a different strand).

Figure 2:
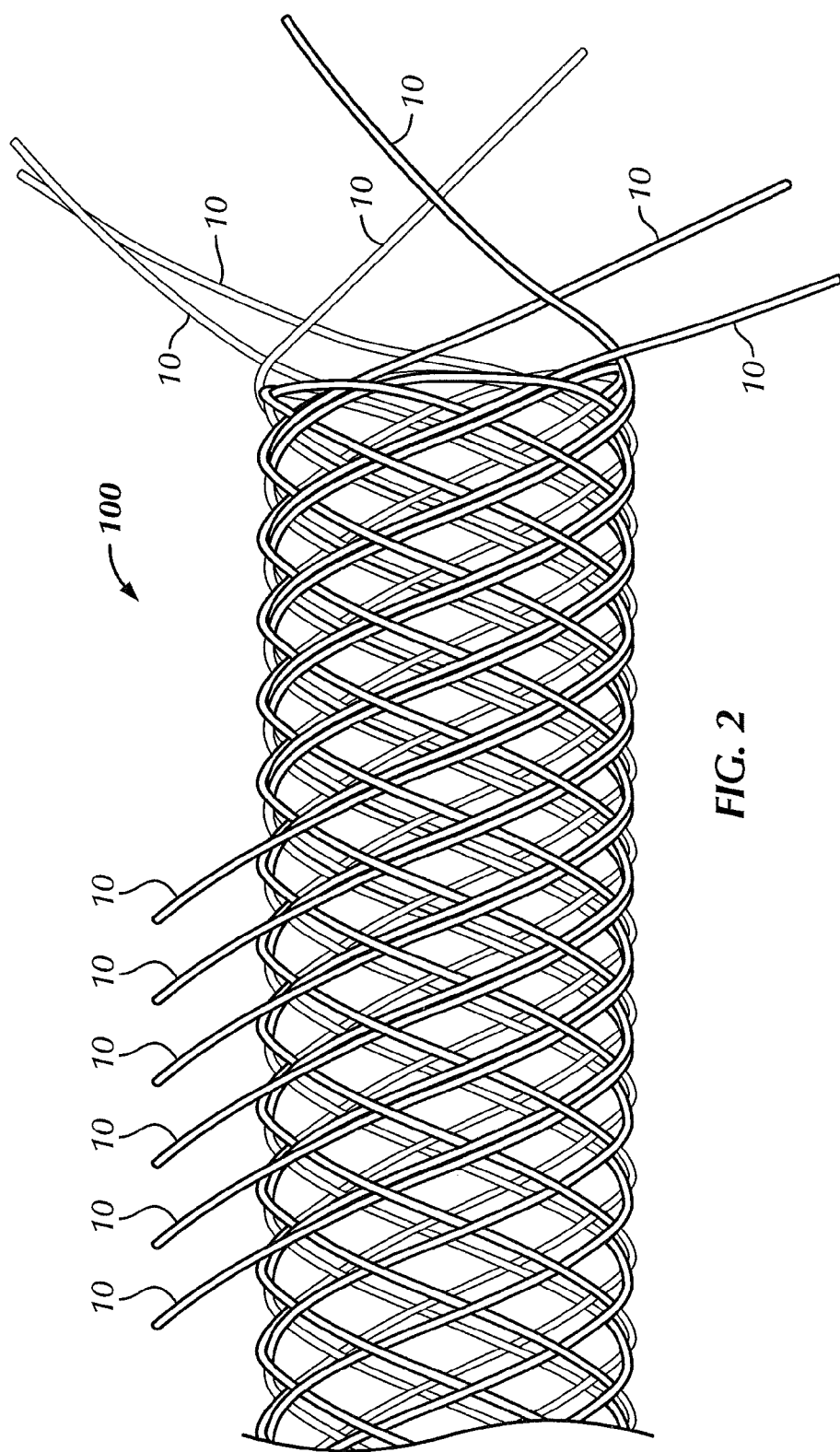
FIG. 2 shows an example of a portion of a device that is being configured for insertion into an anatomical structure, and at a stage of creation where half the free strand ends have been backbraided and the other half remain at one end of the device.

After this heat treatment, the device can be immediately quenched in deionized water until cool. Next, the free strand ends of the device can be backbraided as desired and then baked according to the information in the same table and immediately quenched in deionized water until cool. FIG. 2 shows device 100 after half of the twelve loose strand ends have been backbraided.

Figure 3:
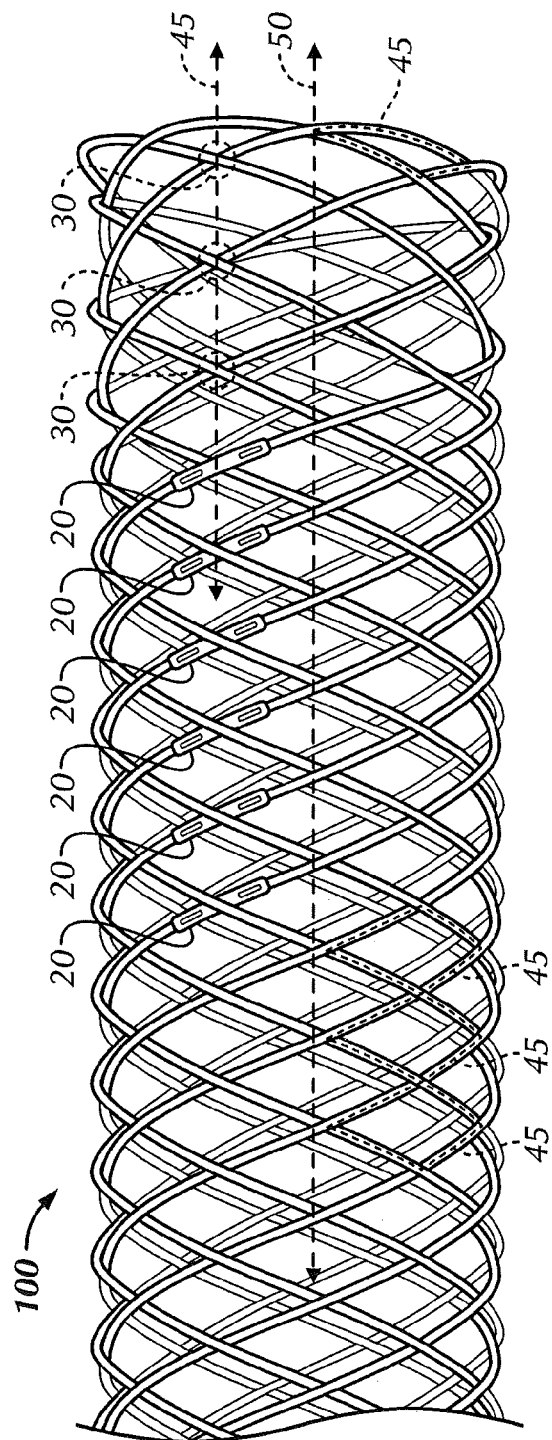
FIG. 3 shows an example of a portion of a device after the weaving reflected in FIG. 1 and the backbraiding reflected in FIG. 2 and that includes coupling structures equal in number to the strands used to create it. Specifically, one coupling structure has been laser welded to each of six different pairs of substantially-aligned strand end portions of the device (for a total of six coupling structures).

Next, one or more coupling structures (e.g., coupling structures that include nickel and titanium, such as 55.8 percent by weight of the total composition and titanium as the balance of the total composition) may be coupled to strand end portions of the woven device at any desired location along the length of the device. The device may be loaded onto a mandrel before the coupling structure(s) are positioned so that the internal diameter of the device is accurately set. Once the coupling structures have been positioned as desired, they can be secured to the strand end portions using any suitable technique, such as laser welding (which is described in more detail below). FIGS. 3-4B show examples of device 100 after coupling structures 20 have each been placed into contact with a pair of strand end portions and then welded to those strand end portions using laser welding as described below. FIG. 5, depicts the two device ends 102 and 104 of a version of device 100 created through the weaving, backbraiding, and coupling structure securing techniques that produced the devices shown in FIGS. 1-4B and 6-9, and shows that device ends 102 and 104 (device end 104 is the device end nearest the coupling structures that were used) are each defined by strand bends 40 (not all of which are labeled) that all have a substantially similar shape.

Figure 4A:
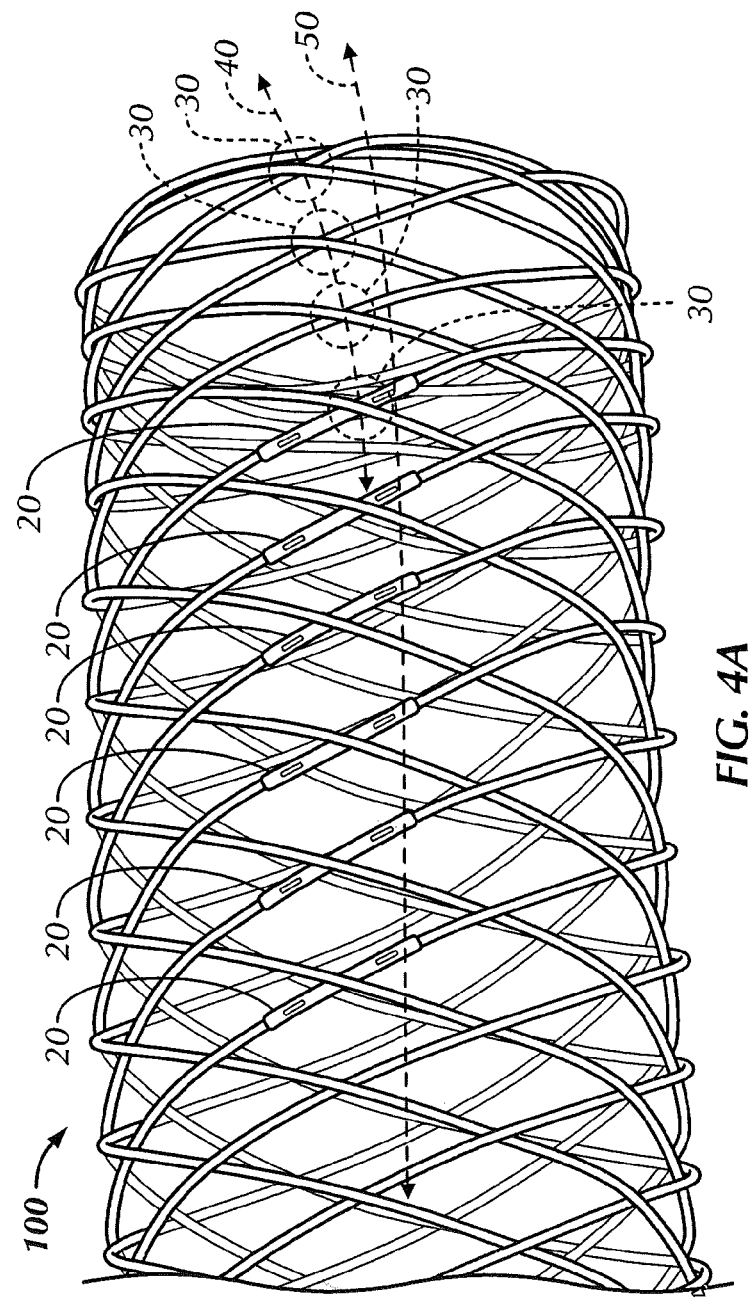
FIGS. 4A and 4B show examples of portions of other devices similar to the one shown in FIG. 3.
Figure 4B:
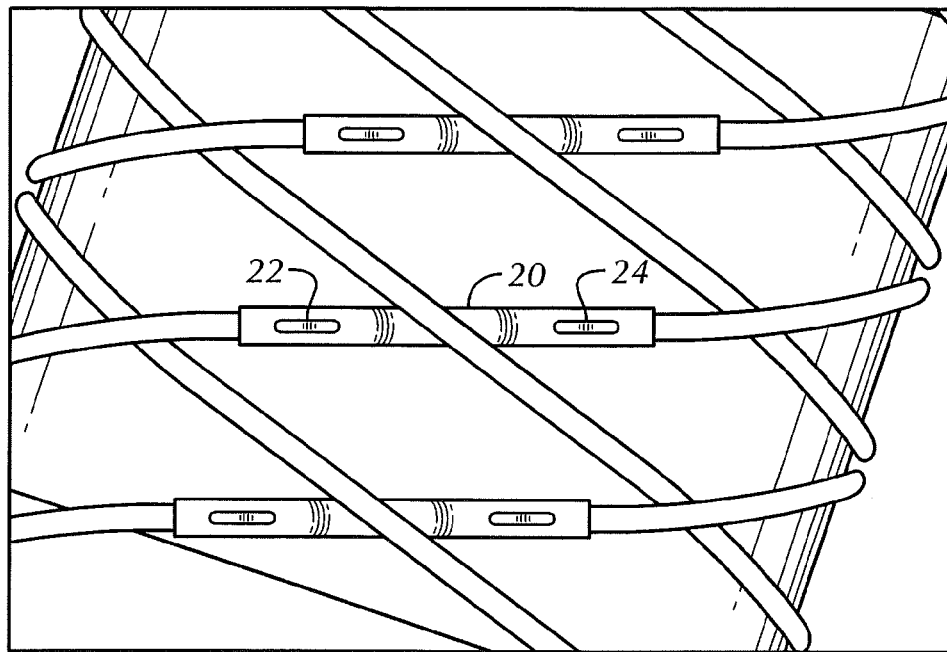
Figure 5:
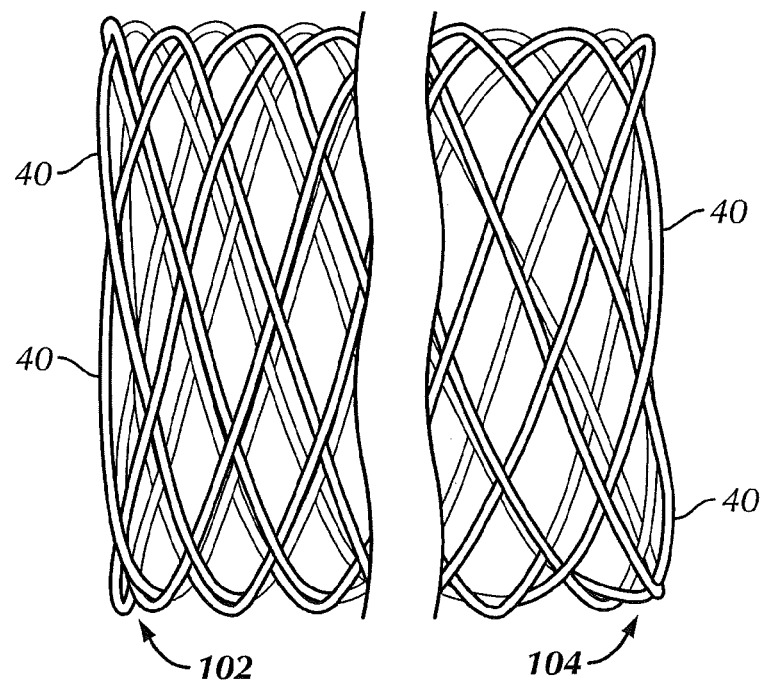
FIG. 5 shows the configuration of the device ends (and the similarity of the strand bends that define them) of a device similar to the one shown in FIGS. 3 and 4.

As shown in FIGS. 3 and 4A, in some embodiments, the coupling structure nearest to a particular device end (e.g., the right-most coupling structure 20 shown in these figures) may be spaced apart from that device end by at least one strand crossing or more. In the embodiment shown in these figures, the right-most coupling structure 20 that is depicted is spaced apart from the depicted device end by at least three strand crossings (which are designated by a circle marked 30) taken along a line 40 that is substantially parallel to longitudinal axis 50 of device 10. This right-most coupling structure is spaced apart from the depicted device end by at least one device opening or more; in particular, by at least three device openings (device openings 45 have been outlined elsewhere in the figure to show that such openings (also characterizable as mesh openings) are defined by strand crossings and, in particular, four strand crossings except for the end-most rows of device openings, which are defined by only three strand crossings (thus, all the device openings of the version of device 100 shown in this figure are defined by at least three strand crossings)). Furthermore, this right-most coupling structure forms the fourth strand crossing 30 along line 40 from the depicted device end, and is positioned beneath a strand of device 10 that crosses over it. Each of the other coupling structures 20 is likewise positioned beneath a strand of device 10 that crosses over it. Prior to the securing, the strand ends to which a given coupling structure is secured may be cut (as necessary) so as to be substantially centered beneath the strand that will pass over that coupling structure; consequently, the coupling structure will be substantially centered at the crossing it, in part, defines, as is true of the coupling structures 20 shown in FIGS. 3-4B.

Figure 6:
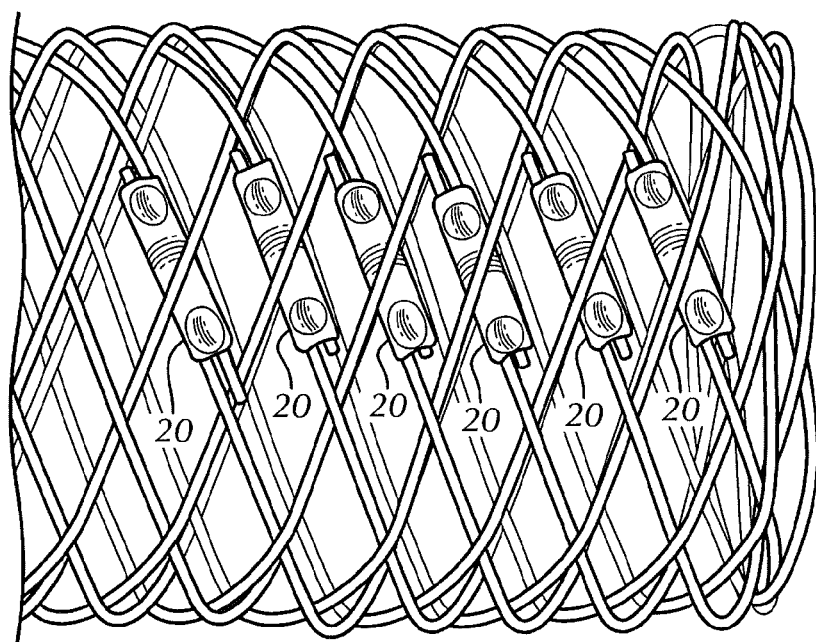
FIG. 6 shows an example of a portion of a device having coupling structures that are axially-aligned and that secure two strand end portions each in overlapping relationship.
Figure 7:
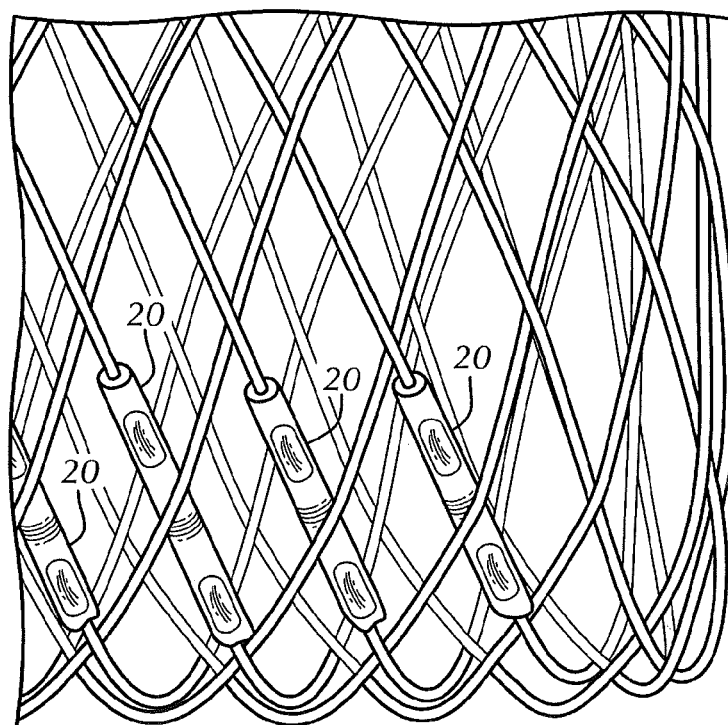
FIG. 7 shows an example of a portion of a device having coupling structures that are axially-aligned and that secure two substantially-aligned strand end portions each.
Figure 8:
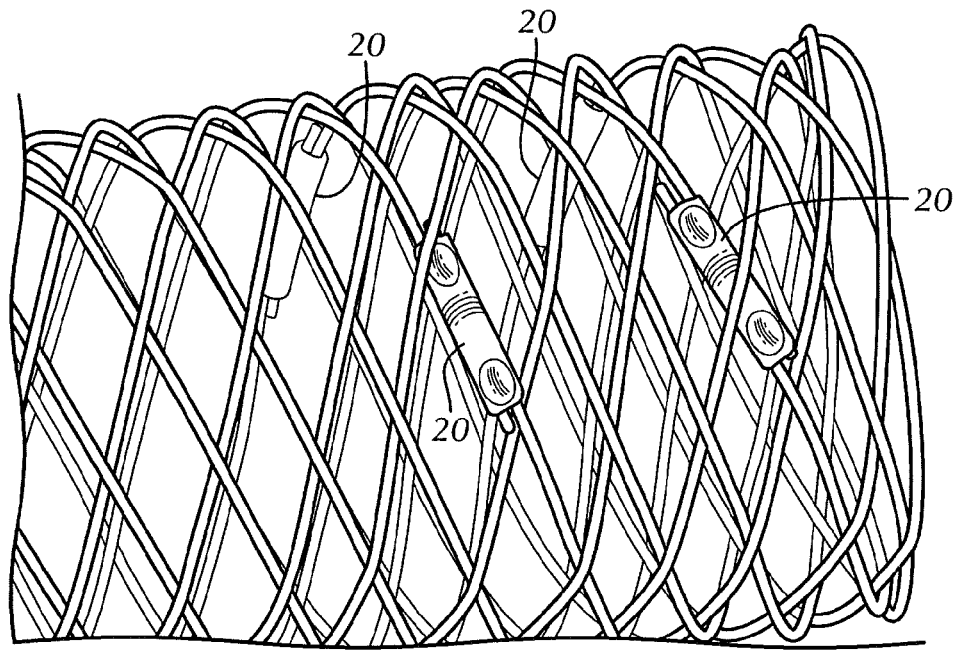
FIG. 8 shows an example of a portion of a device similar to the one shown in FIG. 6, except that adjacent coupling structures are spaced apart from each other around the circumference of the device. Two of the coupling structures that are farthest from the viewer are labeled.
Figure 9:
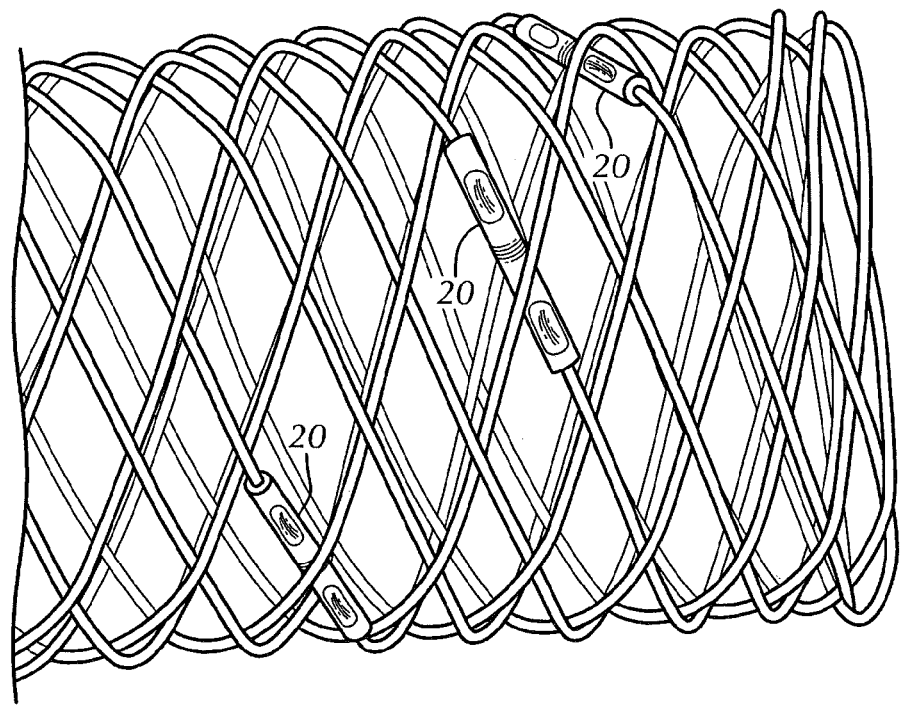
FIG. 9 shows an example of a portion of a device similar to the one shown in FIG. 7, except that adjacent coupling structures are spaced apart from each other around the circumference of the device.

The coupling structures that are used (for stents, the number of coupling structures will preferably equal the number of strands) may be axially aligned as are coupling structures 20 shown in FIGS. 3, 4A, and 4B and in FIGS. 6 and 7, or they may be spaced apart from each other axially and positioned around the circumference of the device, as are coupling structures 20 shown in FIGS. 8 and 9. The cutter used to cut the strand ends may be an Erem® cutter Model 576TX (carbide cutter) or 503ETST (oblique head carbide cutter), which are available from Cooper Hand Tools (Cooper Industries, LLC). Given the small size of the device, a microscope may be employed during the strand end cutting and coupling structure placement.

Figure 10A:
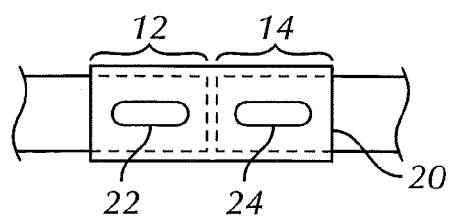
FIG. 10A depicts one coupling structure secured to two strand end portions that are substantially aligned.
Figure 10B:
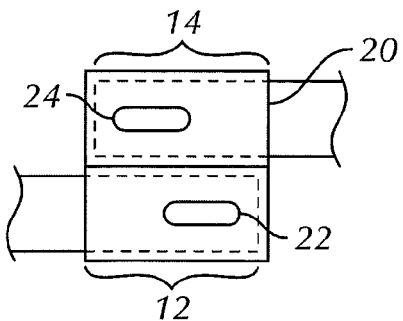
FIG. 10B depicts one coupling structure secured to two strand end portions that overlap with each other.
Figure 10C:
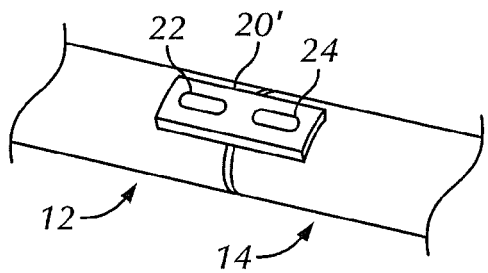
FIG. 10C depicts another embodiment of a coupling structure that is secured to two strand end portions that are substantially aligned.

Examples of coupling structures for joining or coupling two strand ends, which can be of different strands or the same strand, and example arrangements of strand end portions secured by them are shown in FIGS. 10A-10C. FIG. 10A shows coupling structure 20 secured to strand end portions 12 and 14 in a butt joint or butt configuration; as a result of this arrangement, strand end portions 12 and 14 are substantially aligned with each other. Coupling structure 20 is secured to strand end portion 12 by a weld that forms a first welded region 22 and to strand end portion 14 by a weld that forms a second welded region 24. As shown, first welded region 22 is not connected to second welded region 24 by another welded region; the two welded regions are spaced apart from each and separate. Furthermore, the two strand end portions shown in this figure are not in direct contact with each other (there is a slight gap between their ends), though in other embodiments they are in direct contact with each other. The version of coupling structure 20 shown in FIG. 10A has a passageway that exists prior to the coupling structure being secured to either of the strand end portions, and the passageway is sized to receive one device strand.

FIG. 10B shows coupling structure 20 secured to strand end portions 12 and 14 in lap joint or lap configuration; this configuration also may be characterized as overlapping. As a result, the two strand end portions are positioned beside each other rather than end-to-end. Though there is a small gap shown between them in this embodiment, in other embodiments there is direct side-to-side contact between them. The two welded regions 22 and 24 share the same characteristics as those in the FIG. 10A embodiment: they are not connected to each other by another welded region; they are spaced apart from each and separate. Although the welds that produced the two welded regions illustrated schematically in FIG. 10B are directed to only one strand end portion, each, they could both also be applied to both strand end portions, as were the welds that produced the welded regions shown in, for example, FIG. 6. The version of coupling structure 20 shown in FIG. 10B has a passageway that exists prior to the coupling structure being secured to either of the strand end portions, and the passageway is sized to receive two device strands.

FIG. 10C shows another embodiment of one of the present coupling structures, coupling structure 20', which is secured to first strand end portion 12 and to second strand end portion 14 by two welds that form first and second welded regions 22 and 24. Coupling structure 20' does not have a passageway; instead, it is configured as a portion of a tubular structure (e.g., as a strip with an arc, though in other embodiments the strip is flat).

Figure 11A:
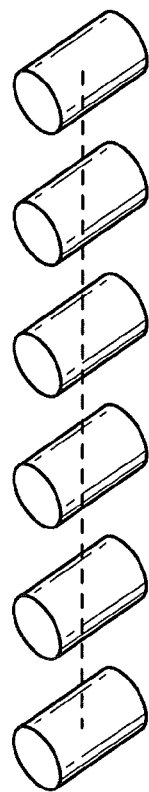
FIGS. 11A and 11B are schematic representations showing different example arrangements of coupling structures for a device such as a woven stent.
Figure 11B:
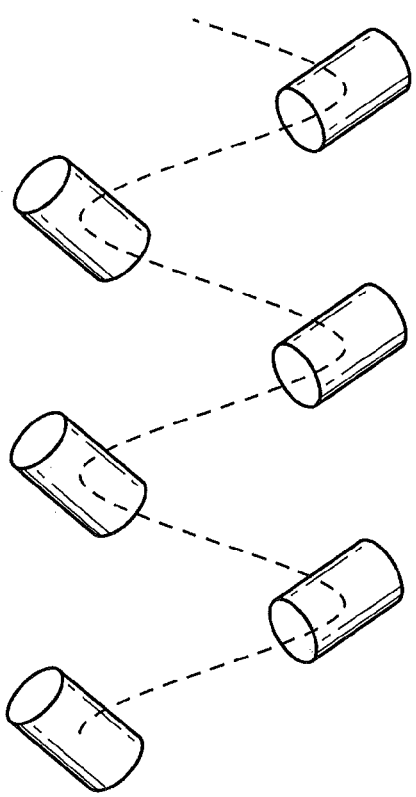

FIG. 11A is a schematic representation showing that the coupling structures 20 for a given device can be axially aligned. FIG. 11B shows they can be helically arranged, which is one way of offsetting them axially and circumferentially (such as at 60 degree intervals) from each other.

Figure 12:
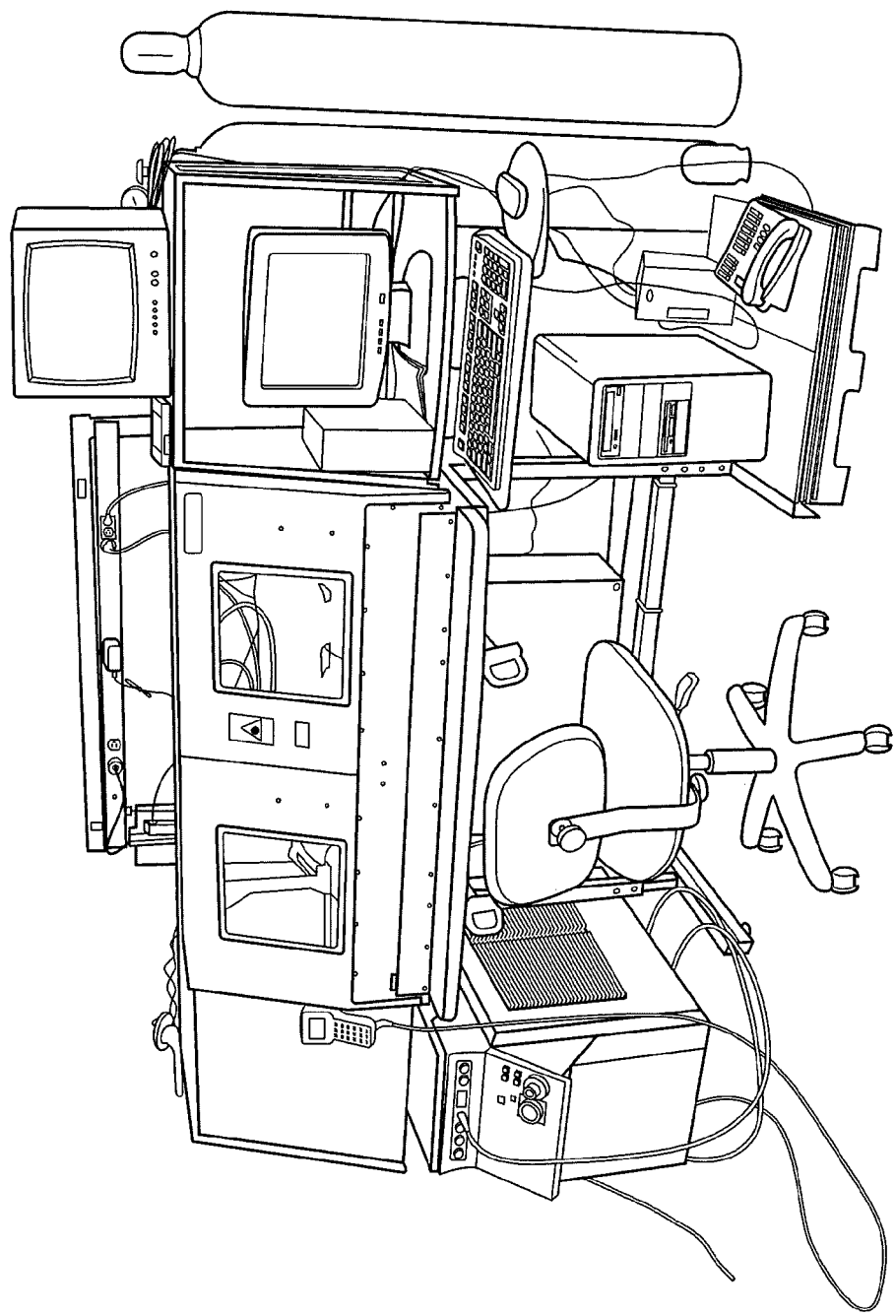
FIG. 12 shows an example of a laser welding system that can be used to create the devices shown in FIGS. 2-9.

For woven stents made from nitinol wires (such as those that include 56.0 percent nickel by weight of the total composition and titanium as the balance of the total composition), coupling structures made from the same type of nitinol (such as 55.8 percent nickel by weight of the total composition and titanium as the balance of the total composition) can be used to couple the ends of different strands using laser welding, such as pulsed laser welding. An example of a suitable laser welding system is shown in FIG. 12, and includes a LASAG pulsed Nd:YAG (Neodymium: Yttrium Aluminum Garnet) "EasyWelder" laser system from the SLS 200 series (Lasag, Switzerland).

Figures 13, 14A:
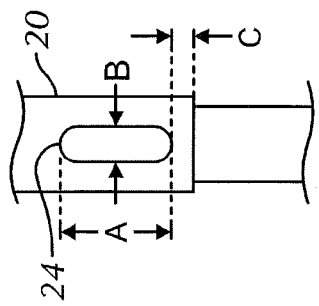
FIG. 13 is a table providing example inner diameter, outer diameter and length dimensions of nitinol coupling structures that can be used for a given diameter nitinol wire size of a given size of six-strand woven stent, and further provides example settings for the LASAG welding system identified below (scfh stands for cubic feet per hour under standard conditions).
FIG. 14A is a detail view showing certain dimensions of a welded region created by a weld that secures the depicted coupling structure to the depicted strand.

For a stent made from six nitinol wires (nickel—56.0 percent by weight of the total composition; titanium—balance of the total composition), six nitinol coupling structures (nickel—55.8 percent by weight of the total composition; titanium—balance of the total composition) may be used. The table in FIG. 13 provides example inner diameter, outer diameter and length dimensions of nitinol coupling structures that can be used for a given diameter nitinol wire size of a given size of six-strand woven stent, and further provides example settings for the LASAG welding system identified above (scfh stands for cubic feet per hour under standard conditions).

The following is a brief description of how coupling structures are secured to the pairs of wire end portions of a heat-treated (according to the technique described above), six-wire woven nitinol stent through a process that is at least partially automated (and in other embodiments fully automated) using the LASAG welding system described above:

the stent has been partially braided back (e.g., by hand), meaning that six of the 12 wire ends are braided back into the stent;

starting at any suitable wire crossing (e.g., the fourth or fifth wire crossing from the end that has been braided back), the wire ends are cut as described above such that the ends of the wires come into contact under the crossing wire;

the coupling structures are loaded onto the wire ends and centered about the crossing wire while on a mandrel so that the internal diameter of the stent is accurately set;

the coupling region of the stent is secured to the mandrel with a spring loaded clip to prevent relative motion between the stent and mandrel, to accurately set the internal diameter of the stent, and to maintain the proper placement of the wire end portions within the coupling structures;

the mandrel mounted and secured stent is then placed in the laser welding system and the first coupling structure is aligned with the horizontal crosshair on the view screen of the system;

the welding program for the size of stent to be welded (examples provided below) is invoked; and the operator is prompted to align the crosshairs with the upper-left corner of the coupling. Once aligned, the operator presses the start button and the left weld bead is created. The system then moves and prompts the operator to align the crosshairs to the upper-right corner. Once aligned, the operator presses the start button and the right weld bead is created. The system then moves to the upper-left corner of the second coupling and the process is repeated. This continues until all 12 welds are completed.

Dimensions for welded region 24 of a given coupling structure 20 of one of the present devices (specifically, a woven stent such as those shown in FIGS. 1-4B) are depicted in FIG. 14A and example values for those dimensions are set forth in FIG. 14B. Table 2 below provides example values for the dimensions of a tubular coupling structure corresponding to the "Coupling Structure Code" set forth in FIG. 14B:

TABLE 2

| Coupling Structure Code | Coupling Structure Inner Dia. (in.) | Coupling Structure Outer Dia. (in.) | Coupling Structure Length (in.) |
| --- | --- | --- | --- |
| -01 | 0.0070 | 0.0100 | 0.070 |
| -02 | 0.0070 | 0.0100 | 0.080 |
| -03 | 0.0075 | 0.0105 | 0.100 |
| -04 | 0.0085 | 0.0120 | 0.120 |
| -05 | 0.0085 | 0.0120 | 0.150 |

Unless otherwise set forth, the tolerances for the values in FIG. 14B are as follows: X.=±1; .X=±0.5; .XX=±0.25; .XXX=±0.125. Unless otherwise set forth, the tolerances for the values in Table 2 are as follows: .X=±0.030; .XX=±0.010; .XXX=±0.005.

Thus, taking the first row of FIG. 14B as an example, a given stent with an internal diameter of 4.0 mm and a length of 40 mm made from nitinol wires (such as those described above) having 0.006 inch diameters could be made with tubular coupling structures (code −01) that each have an internal diameter of 0.0070 inches, an outer diameter of 0.0100 inches, and a length of 0.070 inches, with dimensions A, B, and C of the welded region produced by a laser weld that secures that coupling structure to one of the specified wires having the dimensions of A=0.010 inches, B=0.005 inches, and C=0.010 inches.

The following routines written in industry-standard NC (numerical code) can be used to program the LASAG welding system identified above for use in creating butt-coupled joints using the coupling structures described above for the various sizes of nitinol stents (formed from using the nickel-titanium mixture described above) recited before each routine:

| 4 mm ID stent |
| --- |

```
;4mm Stent Welding Program
M61                ;Laser Remote Control
; Welding Parameters
C101 Q10           ;FREQUENCY 10 HZ
C102 Q0.25         ;PULSE LENGTH 0.25ms
C108 Q200          ;Peak Power 200 W
C111 Q120          ;A-Scale 120
M51                ;MONITOR LASER OK
;Move Laser to common work place
G90                ; Absolute Coordinate
F50                ; Feed Rate
```

| 4 mm ID stent | |
|---|---|
| X3.93 Y-4.6 | ; Locate fixture and part |
| Z-2.656 | ; Adjust Focus |
| ; Weld six couplings | |
| M26 H152 | ; Reset Door |
| M98 P2 | ; Goto Subroutine 1 - 1st Coupling |
| F4 | ; Fast Feed for inter move |
| X-.040 Y.037 | ; Move back to relative 0,0 |
| M98 P2 | ; Goto Subroutine 1 - 2nd Coupling |
| F4 | ; Fast Feed for inter move |
| X-.040 Y.037 | ; Move back to relative 0,0 |
| M98 P2 | ; Goto Subroutine 1 - 3rd Coupling |
| F4 | ; Fast Feed for inter move |
| X-.040 Y.037 | ; Move back to relative 0,0 |
| M98 P2 | ; Goto Subroutine 1 - 4th Coupling |
| F4 | ; Fast Feed for inter move |
| X-.040 Y.037 | ; Move back to relative 0,0 |
| M98 P2 | ; Goto Subroutine 1 - 5th Coupling |
| F4 | ; Fast Feed for inter move |
| X-.040 Y.037 | ; Move back to relative 0,0 |
| M98 P2 | ; Goto Subroutine 1 - 6th Coupling |
| ;Go Back to common work place | |
| G90 | ; Absolute Coordinate |
| F50 | ; Feed Rate |
| X3.93 Y-4.6 | ; Locate fixture and part |
| M25 H152 | ; Open Door |
| M02 | ; End of NC |
| ; /*------ End of Program ------- */ | |
| ; Coupling Weld Subroutine | |
| O2 | ; Welding Routine |
| F1 | ; Feed Rate |
| G05Q1 | ; Jog with Pause / Move to Upper Left Corner |
| G91 | ; Incremental Coordinates |
| M8 | ; Gas On |
| G4F.5 | ; Dwell for .5 seconds |
| X0.008 Y-.004 | ; Offset from corner of coupling |
| M71 | ; Laser Processing with Sync. feed |
| X0.015 | ; Weld left bead = .015: |
| M70 | ; Stop laser processing |
| X0.058 Y.0045 | ; Index to Right Upper Corner |
| G05Q1 | ; Jog with Pause / Adjust to Upper Right Corner |
| X-0.008 Y-.004 | ; Offset from right corner of coupling |
| M71 | ; Laser Processing with Sync. feed |
| X-0.015 | ; Weld bead = .015: |
| M70 | ; Stop laser processing |
| M9 | ; Gas off |
| M99 | ; Return |

| 5 mm ID stent | |
|---|---|
| ;5mm Stent Welding Program | |
| M61 | ;Laser Remote Control |
| ; Welding Parameters | |
| C101 Q10 | ;FREQUENCY 10 HZ |
| C102 Q0.25 | ;PULSE LENGTH 0.25ms |
| C108 Q200 | ;Peak Power 200 W |
| C111 Q120 | ; A-Scale 120 |
| M51 | ;MONITOR LASER OK |
| ; Move to common work place | |
| G90 | ; Absolute Coordinate |
| F50 | ; Feed Rate |
| X3.93 Y-4.6 | ; Locate fixture and part |
| Z-2.656 | ; Adjust Focus |
| ; Weld six couplings | |
| M26 H152 | ; Reset Door |
| M98 P2 | ; Goto Subroutine 1 - 1st Coupling |
| F4 | ; Fast Feed for inter move |
| X-.040 Y.041 | ; Move back to relative 0,0 |
| M98 P2 | ; Goto Subroutine 1 - 2nd Coupling |
| F4 | ; Fast Feed for inter move |
| X-.040 Y.041 | ; Move back to relative 0,0 |
| M98 P2 | ; Goto Subroutine 1 - 3rd Coupling |
| F4 | ; Fast Feed for inter move |
| X-.040 Y.041 | ; Move back to relative 0,0 |
| M98 P2 | ; Goto Subroutine 1 - 4th Coupling |
| F4 | ; Fast Feed for inter move |
| X-.040 Y.041 | ; Move back to relative 0,0 |
| M98 P2 | ; Goto Subroutine 1 - 5th Coupling |
| F4 | ; Fast Feed for inter move |
| X-.040 Y.041 | ; Move back to relative 0,0 |
| M98 P2 | ; Goto Subroutine 1 - 6th Coupling |
| ;Go Back to common work place | |
| G90 | ; Absolute Coordinate |
| F50 | ; Feed Rate |
| X3.93 Y-4.6 | ; Locate fixture and part |
| M25 H152 | ; Open Door |
| M02 | ; End of NC |
| ; Coupling Weld Subroutine | |
| O2 | ; Welding Routine |
| F1 | ; Feed Rate |
| G05Q1 | ; Jog with Pause / Move to Upper Left Corner |
| G91 | ; Incremental Coordinates |
| M8 | ; Gas On |
| G4F.5 | ; Dwell for .5 seconds |
| X0.010 Y-.004 | ; Offset from corner of coupling |
| M71 | ; Laser Processing with Sync. feed |
| X0.015 | ; Weld left bead = .015: |
| M70 | ; Stop laser processing |
| X0.055 Y.0045 | ; Index to Right Upper Corner |
| G05Q1 | ; Jog with Pause / Adjust to Upper Right Corner |
| X-0.010 Y-.004 | ; Offset from right corner of coupling |
| M71 | ; Laser Processing with Sync. feed |
| X-0.015 | ; Weld bead = .015: |
| M70 | ; Stop laser processing |
| M9 | ; Gas off |
| M99 | ; Return |

| 6 mm ID stent | |
|---|---|
| ;6mm Stent Welding Program | |
| M61 | ;Laser Remote Control |
| ; Welding Parameters | |
| C101 Q10 | ;FREQUENCY 10 HZ |
| C102 Q0.3 | ;PULSE LENGTH 0.3ms |
| C108 Q300 | ;Peak Power 200 W |
| C111 Q100 | ;A-Scale 100 |
| M51 | ;MONITOR LASER OK |
| ; Move to common work place | |
| G90 | ; Absolute Coordinate |
| F50 | ; Feed Rate |
| X3.93 Y-4.6 | ; Locate fixture and part |
| Z-2.6716 | ; Adjust Focus |
| ; Weld six couplings | |
| M26 H152 | ; Reset Door |
| M98 P2 | ; Goto Subroutine 1 - 1st Coupling |
| F4 | ; Fast Feed for inter move |
| X-.060 Y.045 | ; Move back to relative 0,0 |
| M98 P2 | ; Goto Subroutine 1 - 2nd Coupling |
| F4 | ; Fast Feed for inter move |
| X-.060 Y.045 | ; Move back to relative 0,0 |
| M98 P2 | ; Goto Subroutine 1 - 3rd Coupling |
| F4 | ; Fast Feed for inter move |
| X-.060 Y.045 | ; Move back to relative 0,0 |
| M98 P2 | ; Goto Subroutine 1 - 4th Coupling |
| F4 | ; Fast Feed for inter move |
| X-.060 Y.045 | ; Move back to relative 0,0 |
| M98 P2 | ; Goto Subroutine 1 - 5th Coupling |
| F4 | ; Fast Feed for inter move |
| X-.060 Y.045 | ; Move back to relative 0,0 |
| M98 P2 | ; Goto Subroutine 1 - 6th Coupling |
| ; Go Back to Common work place | |
| G90 | ; Absolute Coordinate |
| F50 | ; Feed Rate |
| X3.93 Y-4.6 | ; Locate fixture and part |
| M25 H152 | ; Open Door |
| M02 | ; End of NC |
| ; Coupling Weld Subroutine | |
| O2 | ; Welding Routine |
| F1 | ; Feed Rate |

6 mm ID stent

| | |
|---|---|
| G05Q1 | ; Jog with Pause / Move to Upper Left Corner |
| G91 | ; Incremental Coordinates |
| M8 | ; Gas On |
| G4F.5 | ; Dwell for .5 seconds |
| X0.010 Y-.005 | ; Offset from corner of coupling |
| M71 | ; Laser Processing with Sync. feed |
| X0.015 | ; Weld left bead = .015: |
| M70 | ; Stop laser processing |
| X0.075 Y.005 | ; Index to Right Upper Corner |
| G05Q1 | ; Jog with Pause / Adjust to Upper Right Corner |
| X-0.010 Y-.005 | ; Offset from right corner of coupling |
| M71 | ; Laser Processing with Sync. feed |
| X-0.015 | ; Weld bead = .015: |
| M70 | ; Stop laser processing |
| M9 | ; Gas off |
| M99 | ; Return |

7 mm ID stent

| | |
|---|---|
| ;7mm Stent Welding Program | |
| M61 | ;Laser Remote Control |
| ; Welding Parameters | |
| C101 Q10 | ;FREQUENCY 10 HZ |
| C102 Q0.3 | ;PULSE LENGTH 0.3ms |
| C108 Q300 | ;Peak Power 200 W |
| C111 Q100 | ;A-Scale 100 |
| M51 | ;MONITOR LASER OK |
| ; Move to common work place | |
| G90 | ; Absolute Coordinate |
| F50 | ; Feed Rate |
| X3.93 Y-4.6 | ; Locate fixture and part |
| Z-2.6716 | ; Adjust Focus |
| ; Weld six couplings | |
| M26 H152 | ; Reset Door |
| M98 P2 | ; Goto Subroutine 1 - 1st Coupling |
| F4 | ; Fast Feed for inter move |
| X-.060 Y.049 | ; Move back to relative 0,0 |
| M98 P2 | ; Goto Subroutine 1 - 2nd Coupling |
| F4 | ; Fast Feed for inter move |
| X-.060 Y.049 | ; Move back to relative 0,0 |
| M98 P2 | ; Goto Subroutine 1 - 3rd Coupling |
| F4 | ; Fast Feed for inter move |
| X-.060 Y.049 | ; Move back to relative 0,0 |
| M98 P2 | ; Goto Subroutine 1 - 4th Coupling |
| F4 | ; Fast Feed for inter move |
| X-.060 Y.049 | ; Move back to relative 0,0 |
| M98 P2 | ; Goto Subroutine 1 - 5th Coupling |
| F4 | ; Fast Feed for inter move |
| X-.060 Y.049 | ; Move back to relative 0,0 |
| M98 P2 | ; Goto Subroutine 1 - 6th Coupling |
| ; Go Back to Common Work Place | |
| G90 | ; Absolute Coordinate |
| F50 | ; Feed Rate |
| X3.93 Y-4.6 | ; Locate fixture and part |
| M25 H152 | ; Open Door |
| M02 | ; End of NC |
| ; Coupling Weld Subroutine | |
| O2 | ; Welding Routine |
| F1 | ; Feed Rate |
| G05Q1 | ; Jog with Pause / Move to Upper Left Corner |
| G91 | ; Incremental Coordinates |
| M8 | ; Gas On |
| G4F.5 | ; Dwell for .5 seconds |
| X0.010 Y-.005 | ; Offset from corner of coupling |
| M71 | ; Laser Processing with Sync. feed |
| X0.015 | ; Weld left bead = .015: |
| M70 | ; Stop laser processing |
| X0.075 Y.005 | ; Index to Right Upper Corner |
| G05Q1 | ; Jog with Pause / Adjust to Upper Right Corner |
| X-0.010 Y-.005 | ; Offset from right corner of coupling |
| M71 | ; Laser Processing with Sync. feed |
| X-0.015 | ; Weld bead = .015: |
| M70 | ; Stop laser processing |
| M9 | ; Gas off |
| M99 | ; Return |

8 mm ID stent

| | |
|---|---|
| ;8mm Stent Welding Program | |
| M61 | ;Laser Remote Control |
| ; Welding Parameters | |
| C101 Q10 | ;FREQUENCY 10 HZ |
| C102 Q0.3 | ;PULSE LENGTH 0.3ms |
| C108 Q300 | ;Peak Power 200 W |
| C111 Q100 | ; A-Scale 100 |
| M51 | ;MONITOR LASER OK |
| ; Move to common work place | |
| G90 | ; Absolute Coordinate |
| F50 | ; Feed Rate |
| X3.93 Y-4.6 | ; Locate fixture and part |
| Z-2.6544 | ; Adjust Focus |
| ; Weld six Couplings | |
| M26 H152 | ; Reset Door |
| M98 P2 | ; Goto Subroutine 1 - 1st Coupling |
| F4 | ; Fast Feed for inter move |
| X-.067 Y.053 | ; Move back to relative 0,0 |
| M98 P2 | ; Goto Subroutine 1 - 2nd Coupling |
| F4 | ; Fast Feed for inter move |
| X-.067 Y.053 | ; Move back to relative 0,0 |
| M98 P2 | ; Goto Subroutine 1 - 3rd Coupling |
| F4 | ; Fast Feed for inter move |
| X-.067 Y.053 | ; Move back to relative 0,0 |
| M98 P2 | ; Goto Subroutine 1 - 4th Coupling |
| F4 | ; Fast Feed for inter move |
| X-.067 Y.053 | ; Move back to relative 0,0 |
| M98 P2 | ; Goto Subroutine 1 - 5th Coupling |
| F4 | ; Fast Feed for inter move |
| X-.067 Y.053 | ; Move back to relative 0,0 |
| M98 P2 | ; Goto Subroutine 1 - 6th Coupling |
| ; Go Back to Common Work Place | |
| G90 | ; Absolute Coordinate |
| F50 | ; Feed Rate |
| X3.93 Y-4.6 | ; Locate fixture and part |
| M25 H152 | ; Open Door |
| M02 | ; End of NC |
| ; Coupling Weld Subroutine | |
| O2 | ; Welding Routine |
| F1 | ; Feed Rate |
| G05Q1 | ; Jog with Pause / Move to Upper Left Corner |
| G91 | ; Incremental Coordinates |
| M8 | ; Gas On |
| G4F.5 | ; Dwell for .5 seconds |
| X0.010 Y-.006 | ; Offset from corner of coupling |
| M71 | ; Laser Processing with Sync. feed |
| X0.015 | ; Weld left bead = .015: |
| M70 | ; Stop laser processing |
| X0.095 Y.006 | ; Index to Right Upper Corner |
| G05Q1 | ; Jog with Pause / Adjust to Upper Right Corner |
| X-0.010 Y-.006 | ; Offset from right corner of coupling |
| M71 | ; Laser Processing with Sync. feed |
| X-0.015 | ; Weld bead = .015: |
| M70 | ; Stop laser processing |
| M9 | ; Gas off |
| M99 | ; Return |

9 mm ID stent

| | |
|---|---|
| ;9mm Stent Welding Program | |
| M61 | ;Laser Remote Control |
| ; Welding Parameters | |
| C101 Q10 | ;FREQUENCY 10 HZ |
| C102 Q0.3 | ;PULSE LENGTH 0.3ms |

9 mm ID stent

```
C108 Q300              ;Peak Power 200 W
C111 Q100              ; A-Scale 100
M51                    ;MONITOR LASER OK
; Move to common work place
G90                    ; Absolute Coordinate
F50                    ; Feed Rate
X3.93 Y-4.6            ; Locate fixture and part
Z-2.6716               ; Adjust Focus
; Weld six Couplings
M26 H152               ; Reset Door
M98 P2                     ; Goto Subroutine 1 - 1st Coupling
F4                     ; Fast Feed for inter move
X-.067 Y.057           ; Move back to relative 0,0
M98 P2                     ; Goto Subroutine 1 - 2nd Coupling
F4                     ; Fast Feed for inter move
X-.067 Y.057           ; Move back to relative 0,0
M98 P2                     ; Goto Subroutine 1 - 3rd Coupling
F4                     ; Fast Feed for inter move
X-.067 Y.057           ; Move back to relative 0,0
M98 P2                     ; Goto Subroutine 1 - 4th Coupling
F4                     ; Fast Feed for inter move
X-.067 Y.057           ; Move back to relative 0,0
M98 P2                     ; Goto Subroutine 1 - 5th Coupling
F4                     ; Fast Feed for inter move
X-.067 Y.057           ; Move back to relative 0,0
M98 P2                     ; Goto Subroutine 1 - 6th Coupling
; Go Back to Common Work Place
G90                    ; Absolute Coordinate
F50                    ; Feed Rate
X3.93 Y-4.6            ; Locate fixture and part
M25 H152               ; Open Door
M02                    ; End of NC
; Coupling Weld Subroutine
O2                     ; Welding Routine
F1                     ; Feed Rate
G05Q1                  ; Jog with Pause / Move to Upper Left Corner
G91                    ; Incremental Coordinates
M8                     ; Gas On
G4F.5                  ; Dwell for .5 seconds
X0.010 Y-.006              ; Offset from corner of coupling
M71                    ; Laser Processing with Sync. feed
X0.015                 ; Weld left bead = .015:
M70                    ; Stop laser processing
X0.095 Y.006           ; Index to Right Upper Corner
G05Q1                  ; Jog with Pause / Adjust to Upper Right Corner
X-0.010 Y-.006             ; Offset from right corner of coupling
M71                    ; Laser Processing with Sync. feed
X-0.015                    ; Weld bead = .015:
M70                    ; Stop laser processing
M9                     ; Gas off
M99                    ; Return
```

10 mm ID stent

```
;10mm Stent Welding Program
M61                    ;Laser Remote Control
; Welding Parameters
C101 Q10               ;FREQUENCY 10 HZ
C102 Q0.3              ;PULSE LENGTH 0.3ms
C108 Q300              ;Peak Power 200 W
C111 Q100              ; A-Scale 100
M51                    ;MONITOR LASER OK
; Move to common work place
G90                    ; Absolute Coordinate
F50                    ; Feed Rate
X3.93 Y-4.6            ; Locate fixture and part
Z-2.6716               ; Adjust Focus
; Weld six Couplings
M26 H152               ; Reset Door
M98 P2                     ; Goto Subroutine 1 - 1st Coupling
F4                     ; Fast Feed for inter move
X-.067 Y.061           ; Move back to relative 0,0
M98 P2                     ; Goto Subroutine 1 - 2nd Coupling
F4                     ; Fast Feed for inter move
X-.067 Y.061           ; Move back to relative 0,0
M98 P2                     ; Goto Subroutine 1 - 3rd Coupling
F4                     ; Fast Feed for inter move
X-.067 Y.061           ; Move back to relative 0,0
M98 P2                     ; Goto Subroutine 1 - 4th Coupling
F4                     ; Fast Feed for inter move
X-.067 Y.061           ; Move back to relative 0,0
M98 P2                     ; Goto Subroutine 1 - 5th Coupling
F4                     ; Fast Feed for inter move
X-.067 Y.061           ; Move back to relative 0,0
M98 P2                     ; Goto Subroutine 1 - 6th Coupling
; Go Back to Common Work Place
G90                    ; Absolute Coordinate
F50                    ; Feed Rate
X3.93 Y-4.6            ; Locate fixture and part
M25 H152               ; Open Door
M02                    ; End of NC
; Coupling Weld Subroutine
O2                     ; Welding Routine
F1                     ; Feed Rate
G05Q1                  ; Jog with Pause / Move to Upper Left Corner
G91                    ; Incremental Coordinates
M8                     ; Gas On
G4F.5                  ; Dwell for .5 seconds
X0.010 Y-.006              ; Offset from corner of coupling
M71                    ; Laser Processing with Sync. feed
X0.015                 ; Weld left bead = .015:
M70                    ; Stop laser processing
X0.095 Y.006           ; Index to Right Upper Corner
G05Q1                  ; Jog with Pause / Adjust to Upper Right Corner
X-0.010 Y-.006             ; Offset from right corner of coupling
M71                    ; Laser Processing with Sync. feed
X-0.015                    ; Weld bead = .015:
M70                    ; Stop laser processing
M9                     ; Gas off
M99                    ; Return
```

It should be understood that the present methods and the devices they produce are not intended to be limited to the particular forms disclosed. Rather, they are to cover all modifications, equivalents, and alternatives falling within the scope of the claims. For example, while the devices illustrated in the figures have been woven from multiple strands, in other embodiments, the present methods could be applied to devices woven or otherwise created from only a single strand of material (such as a nitinol wire). Further, while stents have been shown in the figures, other devices suited for placement in an anatomical structure, such as filters and occluders, could have their free strand ends joined according to the present methods.

The claims are not to be interpreted as including means-plus- or step-plus-function limitations, unless such a limitation is explicitly recited in a given claim using the phrase(s) "means for" or "step for," respectively.

We claim:

1. A device configured for insertion into an anatomical structure, the device comprising:
   a single strand including a strand portion on both sides of a strand bend, each of the strand portions having an end, the strand portions being woven to form a body having:
   a first body end;
   a second body end; and
   a body length between the first body end and the second body end;
   the strand portion ends are secured together to form a joint assembly that is spaced apart from each end of the body and wherein the joint assembly is positioned beneath a strand of the device that crosses over the joint assembly at a strand crossing;

wherein a length of the joint assembly along a longitudinal axis of the joint assembly is between 0.1 percent and 15 percent of the body length.

2. The device of claim 1, wherein the length of the joint assembly is less than 2 percent of the body length.

3. The device of claim 1, wherein the strand portion ends are secured side-by-side.

4. The device of claim 1, wherein the strand portion ends are secured end-to-end.

5. The device of claim 1, wherein the joint assembly is substantially centered beneath the strand that passes thereover.

6. The device of claim 1, wherein the device is configured as a self-expanding stent.

7. The device of claim 1, wherein the joint assembly is nearer to one of the first body end and the second body end than to the other of the first body end and the second body end.

8. The device of claim 1, wherein the joint assembly is spaced apart from each of the first body end and the second body end by at least two strand crossings.

9. The device of claim 1, wherein the strand portion ends are secured by soldering.

10. The device of claim 1, wherein the strand portion ends are secured by welding.

\* \* \* \* \*